United States Patent [19]

Muller et al.

[11] 4,385,118

[45] * May 24, 1983

[54] FERMENTATION PROCESS

[75] Inventors: Werner C. Muller, Dobbs Ferry, N.Y.; Franklyn D. Miller, Cincinnati, Ohio

[73] Assignee: National Distillers & Chemical Corp., New York, N.Y.

[*] Notice: The portion of the term of this patent subsequent to Jan. 12, 1998, has been disclaimed.

[21] Appl. No.: 313,550

[22] Filed: Oct. 22, 1981

Related U.S. Application Data

[63] Continuation-in-part of Ser. No. 137,074, Apr. 3, 1980, Pat. No. 4,310,629.

[51] Int. Cl.$^3$ ................................................ C12P 7/14
[52] U.S. Cl. .................................... 435/162; 435/813
[58] Field of Search ........................ 435/161, 162, 813

[56] References Cited

U.S. PATENT DOCUMENTS

2,230,318  2/1941  Boinot .................................. 435/162
2,371,208  3/1945  Alzola .................................. 435/162

FOREIGN PATENT DOCUMENTS

2013716  8/1979  United Kingdom ................ 435/162

OTHER PUBLICATIONS

Cysewski et al., Biotechnology and Bioengineering vol. XX, pp. 1421–1444 (1978).

*Primary Examiner*—Lionel M. Shaprio
*Attorney, Agent, or Firm*—Kenneth D. Tremain

[57] ABSTRACT

An improved process is provided for the continuous fermentation of sugar to ethanol in a series of fermentation vessels featuring yeast recycle which is independent of the conditions of fermentation occurring in each vessel at a particular point in time. The process facilitates the management of yeast levels in each fermentation vessel so as to provide an optimum overall rate of ethanol production.

17 Claims, 1 Drawing Figure

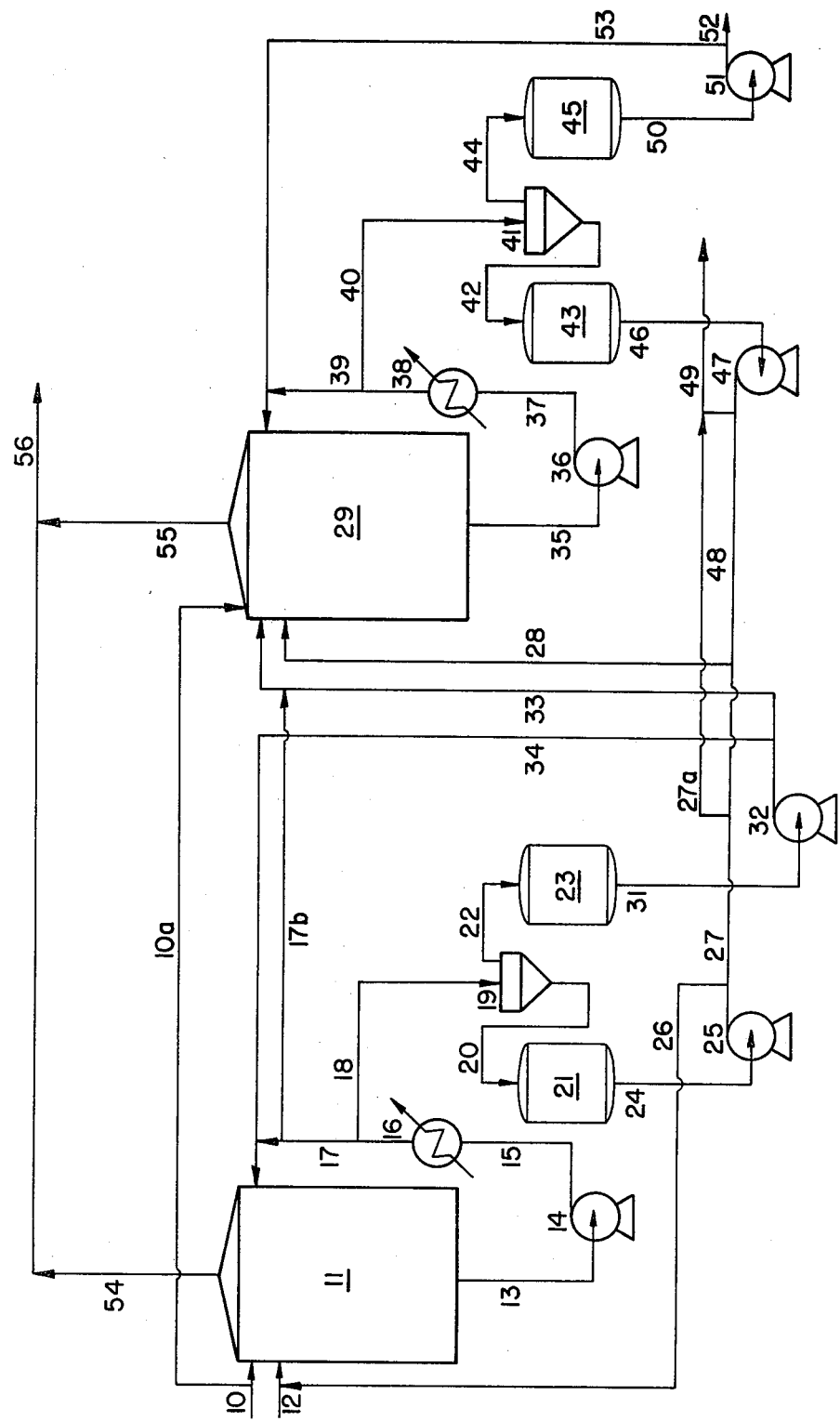

FERMENTATION PROCESS

CROSS REFERENCE TO RELATED APPLICATION

This application is a continuation-in-part of commonly assigned copending U.S. Pat. application Ser. No. 137,074 filed Apr. 3, 1980, now Pat. No. 4,310,629, issued Jan. 12, 1982, the contents of which are incorporated by reference herein.

BACKGROUND OF THE INVENTION

1. Field of the Invention

This invention relates to ethanol fermentation and more particularly to processes for the continuous fermentation of ethanol in a series of fermentation vessels provided with means for recycling fermenting organisms.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentation sugar (liquefaction and saccharification), the fermentation of sugar to a dilute solution of ethanol ("beer") and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy as possible so as to maximize the energy return for the amount of ethanol produced and enhance the standing of the ethanol as an economically viable replacement for petroleum based raw materials. To date, however, relatively little concern has been given to the energy requirements for manufacturing ethanol from biomass and consequently, little effort has been made to minimize the thermal expenditure for carrying out any of the discrete operations involved in the manufacture of ethanol from vegetative sources.

The substitution of alcohol for at least a portion of petroleum based fuels is particularly critical for developing economies where proven domestic petroleum reserves are limited, such as in India and Brazil and these nations have therefore increasingly emphasized the production of alcohol from vegetative sources.

Processes for the continuous fermentation of sugars to provide alcohol and ethanol fermentation processes featuring yeast recycle are known (viz., U.S. Pat. Nos. 1,201,062; 2,054,736; 2,063,223; 2,122,939; 2,146,326; 2,169,244; 2,230,318; 2,272,982; 2,285,130; 2,155,134; 2,371,208; 2,657,174; 2,676,137; 2,967,107; 3,015,612; 3,078,166; 3,093,548; 3,177,005; 3,201,328; 3,207,605; 3,207,606; 3,219,319; 3,234,026; 3,413,124; 3,528,889; 3,575,813; 3,591,454; 3,658,647; 3,676,640; 3,705,841; 3,737,323; 3,940,492; and, 3,984,286; "Process Design and Economic Studies of Alternative Fermentation Methods for the Production of Ethanol", Cysewski, et al. *Biotechnology and Bioengineering*, Vol. xx, pp. 1421–1444 (1978)). In the continuous fermentation process of U.S. Pat. No. 3,234,026 referred to above, a stream of sterile sugar liquor and a quantity of yeast cells are introduced into the first of a series of fermentation vessels wherein initial fermentation is carried out, generally under conditions favoring rapid cell growth. Partial fermentate is continuously withdrawn from the first fermentation vessel and is introduced into a second fermentation vessel wherein fermentation is carried out under conditions favoring rapid conversion of sugar to ethanol. Effluent from the second fermentation is separated into a yeast stream and a substantially yeast-free ethanol ("beer") stream with the yeast stream being recycled to the first fermentation vessel. In this and similar fermentation processes, practical difficulties are encountered in maintaining optimum levels of yeast in both fermentation vessels since the quantities of yeast available for recycle are directly tied to conditions of fermentation which happen to exist in each vessel at a particular point in time. Accordingly, there has heretofore existed a need for a process of continuously fermenting sugar to ethanol in a series of fermentation vessels in which optimum levels of yeast in each vessel are readily and conveniently maintained without regard to the specific fermentation conditions in the vessel at a given moment.

SUMMARY OF THE INVENTION

In accordance with the present invention, in a continuous ethanol fermentation process in which a stream of sterile sugar liquor and a quantity of viable yeast cells are introduced into a first fermentation vessel wherein initial fermentation is carried out under conditions favoring a high level of yeast cell propagation relative to ethanol production, effluent from the first fermentation vessel containing ethanol, sugar and yeast cells is introduced into a second fermentation vessel wherein further fermentation is carried out under conditions favoring a high rate of ethanol production relative to yeast cell propagation and effluent from the second fermentation vessel is separated into a yeast stream and a substantially yeast-free aqueous ethanol stream with the yeast stream being recycled to the first and/or second fermentation vessel, an improvement is provided which comprises: separating effluent from the first fermentation vessel into a first yeast stream and a first substantially yeast-free aqueous ethanol stream; recycling substantially all of the first yeast stream or as much of said yeast stream as necessary to the first fermentation vessel to maintain a high level of yeast cells therein; purging all or part of the remaining portion of the first yeast stream, it any, or introducing at least a part of said remaining portion of the first yeast stream, if any, to the second fermentation vessel with or without introducing yeast-containing effluent from the first fermentation vessel to the second fermentation vessel, it being provided that where no part of the first yeast stream is introduced to the second fermentation vessel, yeast-containing effluent from the first fermentation vessel is introduced to the second fermentation vessel; introducing part or all of the first, substantially yeast-free aqueous ethanol stream into the second fermentation vessel; separating effluent from the second fermentation vessel into a second yeast stream and a second, substantially yeast-free aqueous ethanol stream; and, recycling as much of the second yeast stream as necessary to the second fermentation vessel to maintain a high level of yeast cells therein.

By providing for yeast recycle which is totally independent of fermentation conditions, the present invention makes it possible to readily and conveniently maintain constantly high levels of yeast in both fermentation vessels so as to obtain an optimum overall rate of ethanol production.

The term "first fermentation vessel" shall be understood to refer to one or a series of fermentation vessels wherein relatively high levels of yeast cell propagation are obtained and the term "second fermentation vessel" shall be understood to refer to one or a series of fermentation vessels wherein relatively low levels of yeast cell propagation but relatively high levels of conversion of sugar to ethanol are obtained.

The process of this invention contemplates the known and conventional adjustments of temperature, oxygen level, pH, amount and type of nutrients, etc., as required to maintain optimum yeast cell propagation or ethanol production as the case may be, in the fermentation vessels.

The aqueous ethanol or "beer" containing as much as about 12 weight percent ethanol which is obtained by the process herein can be concentrated employing any of the known and conventional techniques and is advantageously concentrated by the anhydrous distillation process of U.S. Pat. No. 4,256,541 entitled "Production of Anhydrous Ethanol". The stillage bottoms obtained from the rectifying column employed in the aforesaid anhydrous distillation process contains soluble proteins and amino acids of the original beer feed and provide an excellent source of nutrient for yeast employed in the fermentation process herein.

The term "fermentation sugar" should be understood as referring to a single fermentable sugar such as glucose (dextrose), fructose, maltose or sucrose but more commonly will be applicable to these and similar fermentable saccharides in admixture.

BRIEF DESCRIPTION OF THE DRAWING

The accompanying drawing is a diagrammatic flow sheet illustrative of an ethanol fermentation process in accordance with the present invention.

DESCRIPTION OF THE PREFERRED EMBODIMENTS

Referring to the drawing, a sterile aqueous solution of fermentable sugar from any source containing from about 10 to about 40 weight percent sugar, and preferably from about 15 to about 25 weight percent sugar, is taken from storage or directly from a saccharification unit in which the sugar is obtained by the hydrolysis of cellulose or starch, and is introduced through line 10 into a first temperature regulated, agitated fermentation vessel provided with pH control and means for introducing nutrients and the small amounts of oxygen conventionally employed for maintaining proper yeast metabolism during fermentation. Sterile aqueous fermentable sugar can also be introduced, if desired, through lines 10 and 10a into a second fermentation vessel 29 having a construction identical or similar to that of the first. In the event the sugar solution contains more than 20 weight percent sugar, it is preferable to dilute the solution to about this level of sugar, advantageously with the nitrogen-rich still bottoms obtained from an ethanol distillation unit such as described in the aforesaid U.S. Pat. No. 4,256,541. The use of still bottoms when available possesses the two-fold advantage of recycling nitrogen to the fermentation system which would otherwise be lost upon concentration of the ethanol during distillation, and reducing process water consumption by avoiding water build-up in the stillage effluent. In addition to sugar, the foregoing solution may also contain significant amounts of partial hydrolysates (e.g., up to about 40 weight percent of the total carbohydrate present) which can be saccharified to fermentable sugar under the influence of the saccharifying enzyme produced by the fermenting yeast and/or added saccharifying enzyme. To initiate the process, a pumpable slurry of ethanol-producing yeast organisms free of contaminating organisms is conveyed from yeast storage into fermentation vessel 11 through line 12.

The yeast in fermentation vessels 11 and 29 can be maintained at a level of from about 2 to about 8 weight percent, and preferably at a level of from about 3 to about 6 weight percent, of the fermentation medium (based on dry weight of yeast). Once continuous fermentation has started and a steady state has been achieved, there will be no need to add more yeast since sufficient quantities of make-up yeast are grown in fermentation vessel 11. The temperature of the medium in each fermentation vessel is advantageously kept at a level of from about 68° F. to about 104° F., and preferably at a level of from about 86° F. to about 99° F. The pH of each fermentation vessel is similarly regulated and can range from about 3.5 to about 5.5 and preferably from about 4.0 to 4.6. Conditions, themselves known in the art, are so maintained in fermentation vessel 11 as to maintain a relatively high rate of yeast cell propagation and viability therein. In general, it is desirable to maintain a level of viability of at least about 60 percent and preferably, at least about 70 percent, and an ethanol level (by weight) of from about 5 percent to about 8 percent, and preferably from about 6 percent to about 7 percent, in fermentation vessel 11. Aqueous effluent containing ethanol, yeast cells and unconverted fermentable sugar is withdrawn from fermentation vessel 11 through line 13 and is driven by pump 14 through line 15 through cooler 16 (which removes a sufficient amount of heat of fermentation from the effluent to maintain optimum temperature levels in vessel 11) and back to the fermentation vessel through line 17. Optionally, part or all of the effluent from first fermentation vessel 11 can be conveyed to a second fermentation vessel 29; thus, for example, cooled effluent passing through line 17 can be diverted through lines 17b and 33 into second fermentation vessel 29. A portion of the effluent is diverted from line 15 and/or line 17 to where it enters first yeast separator 19. In the embodiment shown, cooled effluent is taken from line 17 to enter first yeast separator 19 through line 18. The yeast separator, which can be a gravity separator, filter or preferably, a centrifuge, separates the fermentate into two streams: a first yeast slurry or "cream" which enters a first yeast slurry holding tank 21 through line 20 and a substantially yeast-free partial fermentate which enters partial fermentate surge tank 23 through line 22. When the amount of yeast in fermentation vessel 11 falls significantly below a predetermined level, as much of the first yeast slurry up to substantially the entire amount thereof is taken from holding tank 21 through line 24 and recycled by pump 25 through line 26 back to first fermentation vessel 11 to restore the amount of yeast to the desired level. Part or all of the remaining portion of the first yeast stream, if any, is delivered by pump 25 through lines 27 and 28 to second fermentation vessel 29. Optionally, part or all of the remaining portion of the first yeast stream, if any, can be purged from the system through lines 27a and 49. In the case where no portion of the first yeast stream is conveyed to second fermentation vessel 29, it is necessary to introduce yeast containing effluent from first fermentation vessel 11 to second fermentation vessel 29, for example, by diverting cooled effluent from line 17 through lines 17b and 33 into said second fermentation vessel. Substantially yeast-free partial fermentate is taken from partial fermentate surge tank 23 through line 31 and is delivered by pump 32 through line 33 to second fermentation vessel 29. A portion of the partial fermentate can also be recycled back to fermentation vessel 11 through line 34 so as to contribute to the maintenance of conditions favoring high yeast cell propagation therein.

Conditions of fermentation in the second fermentation vessel 29 are regulated in a known and conventional manner so as to provide a high level of conversion of the remaining sugar to ethanol. Yeast viability in the second fermentation vessel is preferably maintained at a level of at least about 50 percent and preferably at a level of at least about 60 percent. The ethanol concentration in the second fermentation vessel is desirably kept at a level of from above about 8 weight percent, and preferably, from about 10 to about 12 weight percent, of the fermentation medium therein. Optimum temperature control is obtained by circulating effluent from line 35 by pump 36 through line 37 through cooler 38 and through line 29 back to the second fermentation vessel. A portion of the effluent is routed through line 40 where it is separated by a second yeast separator 41 into a second yeast slurry which enters second yeast slurry holding tank 43 through line 42, and a substantially yeast-free final fermentate which enters final fermentate surge tank 45 through line 44. Yeast slurry is withdrawn from second yeast slurry holding tank 43 through line 46 and recycled by pump 47 through lines 48 and 28 back to second fermentation vessel 29 in amounts necessary to maintain a predetermined high level of yeast cells therein. Excess yeast slurry is purged from the system through line 49. Final fermentate is taken from tank 45 through line 50 and is forced by pump 51 through line 52 to storage or directly to a distillation unit for the recovery of ethanol in concentrated, e.g., anhydrous, form. A portion of final fermentate can also be recycled through line 53 back to second fermentation vessel 29 to help maintain conditions therein favoring high rates of ethanol production. Metabolically evolved carbon dioxide gas containing ethanol is conveyed from each of fermentation vessels 11 and 29 through vent lines 54 and 55, and common line 56 to a carbon dioxide gas absorption tower or scrubber for recovery of the ethanol therein.

The data below represent a typical material balance for an ethanol fermentation process which is capable of producing about 20,000 lb/day of approximately 10 weight percent ethanol.

| | Material Balance For 20,000 lb/Day (10 weight percent) | | | | | | | | | | | |
|---|---|---|---|---|---|---|---|---|---|---|---|---|
| | Process Line | | | | | | | | | | | |
| Component | 10 | 18 | 20 | 22 | 27 | 33 | 40 | 42 | 44 | 49 | 52 | 56 |
| Water (steam) | 161,056 | 226,711 | 67,939 | 158,772 | 3,331 | 158,772 | 264,690 | 111,217 | 158,473 | 3,480 | 158,473 | 428 |
| Ethanol | 32 | 18,311 | 5,487 | 12,824 | 269 | 12,824 | 34,322 | 14,154 | 20,168 | 443 | 20,168 | 307 |
| Glycerol | 6,583 | 11,066 | 3,316 | 7,750 | 162 | 7,750 | 14,440 | 5,955 | 8,485 | 186 | 8,485 | — |
| Glucose | 44,936 | 22,248 | 6,697 | 15,651 | 340 | 15,651 | 674 | 278 | 396 | 9 | 396 | — |
| Maltose | 9,203 | 12,871 | 3,857 | 9,014 | 189 | 9,014 | 15,325 | 6,320 | 9,005 | 198 | 9,005 | — |
| Protein and Fiber | 203 | 3,533 | 3,516 | 17 | 186 | 17 | 6,044 | 6,027 | 17 | 186 | 17 | — |
| Ammonium Sulfate | 1,179 | 1,652 | 497 | 1,155 | 24 | 1,155 | 1,974 | 814 | 1,154 | 25 | 1,154 | — |
| Yeast | — | 18,546 | 18,460 | 86 | 894 | 86 | 28,783 | 28,702 | 81 | 899 | 81 | — |
| Solubles | 264 | 368 | 110 | 258 | 6 | 258 | 439 | 181 | 258 | 6 | 258 | — |
| Carbon Dioxide | — | — | — | — | — | — | — | — | — | — | — | 20,577 |
| Air | — | — | — | — | — | — | — | — | — | — | — | 33 |
| Total | 223,456 | 315,406 | 109,879 | 205,527 | 5,401 | 205,527 | 371,691 | 173,648 | 198,037 | 5,432 | 198,037 | 21,395 |

What is claimed is:

1. In a continuous ethanol fermentation process in which a stream of sterile sugar liquor and a quantity of viable yeast cells are introduced into a first fermentation vessel wherein initial fermentation is carried out under conditions favoring a high level of yeast cell propagation relative to ethanol production, effluent from the first fermentation vessel containing ethanol, sugar and yeast cells is introduced into a second fermentation vessel wherein further fermentation is carried out under conditions favoring a high rate of ethanol production relative to yeast cell propagation and effluent from the second fermentation vessel is separated into a yeast stream and a substantially yeast-free aqueous ethanol stream with the yeast stream being recycled to the first and/or second fermentation vessel, an improvement is provided which comprises:

(a) separating effluent from the first fermentation vessel into a first yeast stream and a first substantially yeast-free aqueous ethanol stream;

(b) recycling substantially all of the first yeast stream or as much of said yeast stream as necessary to the first fermentation vessel to maintain a high level of yeast cells therein;

(c) purging all or part of the remaining portion of the first yeast stream, if any, or introducing at least a part of said remaining portion of the first yeast stream, if any, to the second fermentation vessel with or without introducing yeast-containing effluent from the first fermentation vessel to the second fermentation vessel, it being provided that where no part of the first yeast stream is introduced to the second fermentation vessel, yeast-containing effluent from the first fermentation vessel is introduced to the second fermentation vessel;

(d) introducing part or all of the first, substantially yeast-free aqueous ethanol stream into the second fermentation vessel;

(e) separating effluent from the second fermentation vessel into a second yeast stream and a second, substantially yeast-free aqueous ethanol stream; and, (f) recycling as much of the second yeast stream as necessary to the second fermentation vessel to maintain a high level of yeast cells therein.

2. The process of claim 1 wherein as much of the first, substantially yeast-free aqueous ethanol stream is recycled to the first fermentation vessel as necessary to maintain conditions favoring a high level of yeast cell propagation therein with the remaining portion of the first, substantially yeast-free aqueous ethanol stream being introduced into the second fermentation vessel.

3. The process of claim 1 wherein as much of the second, substantially yeast-free aqueous ethanol stream is recycled to the second fermentation vessel as necessary to maintain a high level of fermentation of sugar to ethanol therein.

4. The process of claim 1 wherein the yeast cell level in the first fermentation vessel and/or the second fermentation vessel is maintained at from about 2 to about 8 weight percent of the fermentation medium therein.

5. The process of claim 1 wherein the yeast cell level in the first fermentation vessel and/or the second fermentation vessel is maintained at from about 3 to about 6 weight percent of the fermentation medium therein.

6. the process of claim 1 wherein the viability of the yeast cells in the first fermentation vessel is maintained at a level of at least about 60 percent.

7. The process of claim 1 wherein the viability of the yeast cells in the first fermentation vessel is maintained at a level of at least about 70 percent.

8. The process of claim 1 wherein the viability of the yeast cells in the second fermentation vessel is maintained at a level of at least about 50 percent.

9. The process of claim 1 wherein the viability of the yeast cells in the second fermentation vessel is maintained at a level of at least about 60 percent.

10. The process of claim 1 wherein fermentation in the first fermentation vessel is carried out until ethanol represents from about 5 to about 8 weight percent of the fermentation medium therein.

11. The process of claim 1 wherein fermentation in the first fermentation vessel is carried out until ethanol represents from about 6 to about 7 weight percent of fermentation medium therein.

12. The process of claim 1 wherein fermentation in the second fermentation vessel is carried out until ethanol represents from above about 8 to about 10 weight percent of the fermentation medium therein.

13. The process of claim 1 wherein substantially all of the first yeast stream is recycled to the first fermentation vessel and yeast-containing effluent from the first fermentation vessel is introduced to the second fermentation vessel.

14. The process of claim 1 wherein only a part of the first yeast stream is recycled to the first fermentation vessel, the entire balance of the remaining portion of the first yeast stream is purged and yeast-containing effluent from the first vessel is introduced to the second fermentation vessel.

15. The process of claim 1 wherein only a part of the first yeast stream is recycled to the fermentation vessel, part of the remaining portion of the first yeast stream is purged and the balance of the remaining portion of the first yeast stream is introduced to the second fermentation vessel with or without yeast-containing effluent from the first fermentation vessel being introduced to the second fermentation vessel.

16. The process of claim 1 wherein only a part of the first yeast stream is recycled to the first fermentation vessel and substantially all of the remaining portion of the first yeast stream is introduced to the second fermentation vessel with or without yeast-containing effluent from the first fermentation vessel being introduced to the second fermentation vessel.

17. The process of claim 1 wherein said second, substantially yeast-free ethanol stream is subjected to distillation for recovery of the ethanol in concentrated form and stillage bottoms containing nutrients useful in yeast metabolism which are obtained from the distillation are introduced into the first fermentation vessel.

* * * * *